United States Patent [19]

Langerbeins et al.

[11] Patent Number: 5,132,449
[45] Date of Patent: Jul. 21, 1992

[54] METHOD FOR THE CATALYTIC VAPOR PHASE OXYDEHYDROGENATION OF ISOBUTYRIC ACID

[75] Inventors: Klaus Langerbeins, Langen; Ruediger Jelitte, Rossdorf; Wolfgang Ruppert, Seeheim-Jugenheim; Gerhard Emig; Otto Watzenberger, both of Erlangen; Thomas Haeberle, Zirndorf, all of Fed. Rep. of Germany

[73] Assignee: Röhm GmbH, Darmstadt, Fed. Rep. of Germany

[21] Appl. No.: 569,559

[22] Filed: Aug. 20, 1990

Related U.S. Application Data

[62] Division of Ser. No. 273,852, filed as PCT/DE88/00144, Mar. 15, 1988, abandoned.

[30] Foreign Application Priority Data

Mar. 17, 1987 [DE] Fed. Rep. of Germany ....... 3708627
Mar. 7, 1988 [DE] Fed. Rep. of Germany ....... 3807363
Mar. 7, 1988 [DE] Fed. Rep. of Germany ....... 3807364

[51] Int. Cl.$^5$ .............................................. C07C 67/30
[52] U.S. Cl. ................................................... 560/214
[58] Field of Search ......................................... 560/211

[56] References Cited

U.S. PATENT DOCUMENTS

| 4,439,621 | 3/1984 | Daniel | 562/599 |
| 4,499,302 | 2/1985 | Moreschini et al. | 562/599 |
| 4,720,575 | 1/1988 | Gruber et al. | 562/599 |
| 4,864,057 | 9/1989 | Pedersen | 562/599 |

FOREIGN PATENT DOCUMENTS

| 1194014 | 9/1985 | Canada . |
| 308865 | 3/1989 | European Pat. Off. . |
| 3145091 | 5/1983 | Fed. Rep. of Germany . |
| 3626255 | 2/1988 | Fed. Rep. of Germany . |

Primary Examiner—Paul J. Killos
Attorney, Agent, or Firm—Donald R. Bentz

[57] ABSTRACT

The invention relates to the stabilization of the activity and/or the reactivation of molybdoheteropoly acid catalysts in vapor-phase oxidations, such as the oxidehydrogenation of isobutyric acid or its lower esters to methacrylic acid or its lower esters, by means of an oxidizing treatment of the catalyst in which compounds of catalyst constituents are added, at temperatures ranging from 200° to 400° C., with an oxygen-containing gas.

The inventive activation measures can be carried out either during the catalytic vapor-phase reaction, such as oxihydrogenation in particular, or intermittently to alternate therewith, and optionally also physically separated in part from each other.

12 Claims, No Drawings

METHOD FOR THE CATALYTIC VAPOR PHASE OXYDEHYDROGENATION OF ISOBUTYRIC ACID

This application is a division of application Ser. No. 07/273,852, filed as PCT/DE88/00144, Mar. 15, 1988, abandoned.

FIELD OF THE INVENTION

The invention relates to a process for preventing the deactivation of, or for regenerating partially deactivated, heteropoly catalysts containing phosphorus, molybdenum and vanadium as essential elements, during their use as oxidation catalysts, and more particularly as catalysts for the oxyhydrogenation of isobutyric acid or its lower esters.

THE PRIOR ART

Heteropoly acids, and particularly heteropoly phosphoric acids of molybdenum such as phosphomolybdic acid, $H_3PMo_{12}O_{40}$, or molybdovanadophosphoric acids such as $H_5PMoV_2O_{40}$ and others, are effective as catalysts in vapor-phase oxidations, as, for example, in the synthesis of unsaturated carboxylic acids from unsaturated aldehydes, or in oxidative dehydrogenations in the vapor phase, as in the preparation of unsaturated carboxylic acids from saturated carboxylic acids.

The heteropoly acids and/or metal salts thereof are preferably used as catalysts deposited on an inert material. (U.S. Pat. Nos. 4,146,574 and 4,370,390.) Such catalysts do not retain for an extended period of time the maximum activities and selectivities which they attained after being broken in, as they should in a commercial process. After a few days or weeks, their effectiveness keeps decreasing.

Japanese patent 81 163 755 describes a process for the recovery of the heteropoly acids from associated catalyst components by means of their extraction with an aqueous medium from partially deactivated catalytic heteropoly acid/carrier combinations. The extraction s followed by a contacting of the extracting solution at higher temperatures with molecular oxygen; or the two steps, extraction and the action of molecular oxygen at higher temperatures, are carried out concurrently. The catalysts are used in the oxyhydrogenation of isobutyric acid to methacrylic acid, for example. Any loss of molybdenum sustained in the use of the heteropoly acid catalysts can be made up for in the recovery process by the addition of molybdenum oxide or of molybdic oxo acid. From the recovered heteropoly acid solutions, catalysts containing $H_5PMo_{10}V_2O_{40}$, for example, are again prepared with carrier materials and reused in oxydehydrogenation.

Published German patent application 36 26 255 describes a process for the regeneration of heteropoly acid catalysts used in the oxydehydrogenation of isobutyric acid or its esters to methacrylic acid or its esters which is characterized in that a catalyst made from phosphomolybdic acid and/or its vanadium derivatives and/or their salts is subjected to an oxidizing treatment with an oxygen-containing gas at temperatures ranging from 200° to 400° C. for regeneration.

These prior-art processes for the regeneration of oxydehydrogenation catalysts based on a heteropoly acid with molybdenum as an essential constituent are afflicted with a number of serious drawbacks. The process of the Japanese patent, for example, which involves extraction, that is, separation from the catalyst carrier, a relatively protracted oxygen treatment, concentration of the extract, redeposition of heteropoly acid on the catalyst carrier, filling of the reactor with catalyst, and renewed start-up of the oxydehydrogenation, is very onerous from the process-engineering standpoint and very time-consuming.

The process of German patent application 36 26 255, on the other hand, is simple from the process-engineering point of view and can be carried out without undue expenditure of time. However, the measures which have to be adopted fall short of restoring the catalyst to the requisite activity and selectivity, and its catalytic effectiveness therefore declines rather rapidly over the operating times imposed by technical and economic considerations.

German patent publication 24 35 031 describes a process for the production of acrylonitrile by ammoxidation of propylene over molybdenum-containing metaloxide catalysts in which the catalyst upon losing activity is regenerated under the conditions of ammoxidation by adding molybdenum-containing carrier to the fluidized bed.

THE OBJECT AND THE INVENTION

The object of the invention is to prevent or considerably retard the progressive deactivation of catalysts made from heteropoly acids of molybdenum during the catalyzed reaction, and more particularly during the oxyhydrogenation of isobutyric acid or its lower esters to the corresponding methacrylic compounds, with a view to securing technically and economically worthwhile operating times for the catalysts used.

It has been found that the reactivation or activity stabilization of the catalysts can be accomplished 1. by introducing catalyst elements in the form of compounds of appropriate elements into the catalyst system, and
2. by an oxidizing treatment at from 200° to 400° C. of the catalysts so replenished, these measures being carried out on the catalysts within the reactor system without removing them, either during or as part of the catalytic oxidation reaction, such as the oxidative dehydrogenation of isobutyric acid, or during the oxidative regeneration of the spent catalysts according to German patent application 36 26 255. However, these measures may also be carried out at different times and on different sites.

It is surprising that the catalyst species which are effective in the oxidation reactions should form from the combined components, that is, from the catalyst fragments and the compounds introduced for replenishment, even at temperatures of from 200° to 400° C. in an oxidizing atmosphere It has been found that in the oxydehydrogenation of isobutyric acid over heteropoly acids of molybdenum, it is this element in particular that is being carried out of the reaction zone. This is probably what accounts in large measure for the rather pronounced decrease in the long-term activity of the catalyst. However, other elements contained in the catalyst, such as vanadium, phosphorus or further catalyst additives, are also being carried off during the oxidation reaction. Experience has shown that normally, that is, when the catalyst does not contain an element known to be relatively volatile, the molybdenum losses considerably exceed the losses of elements other than molybdenum.

It is important for the new process that an effective stabilization or regeneration of the catalyst, whether by reoxidation of the elements which form part of the heteropoly acid catalyst complex, and in particular molybdenum and vanadium and optionally further metal ions, or by re-formation of the heteropoly acid catalyst complex by means of the compounds of catalyst elements introduced in accordance with the invention, such as molybdenum, phosphorus and/or vanadium, and particularly molybdenum and/or phosphorus and optionally further essential heteropoly acid components, be carried out in an oxygen-containing atmosphere.

The invention relates to a process for the stabilization of the activity and/or the regeneration of catalysts made from heteropoly acids containing molybdenum, phosphorus and vanadium as essential elements, and optionally further metallic elements as cations, during their use as oxidation catalysts in vapor-phase reactions, which is characterized in that compounds with catalyst elements are added to the catalyst and that the catalyst is heated to from 200° to 400° C. in an oxygen-containing oxidizing atmosphere.

The invention permits the advantageous regeneration of spent catalyst at temperatures ranging from 200° to 400° C., without the need to resort to technically complicated measures, in practically continuous or continuously/cyclically operated catalytic processes.

The principal catalytic process in which the inventive measures are adopted is the oxidative dehydrogenation of isobutyric acid or its lower esters to methacrylic acid or its lower esters, which is carried out over heteropoly acid catalysts at temperatures ranging from 250° to 400° C.

The invention thus also relates to a process for the regeneration of heteropoly acid catalysts which contain molybdenum, phosphorus and vanadium as essential elements, and optionally further metallic elements as cations, for their use as oxidation catalysts in vapor-phase reactions, and particularly in the oxydehydrogenation of isobutyric acid or its lower esters to methacrylic acid or its lower esters, in which compounds with catalyst constituents are added for regeneration to the catalyst, made from phosphomolybdic acid and/or its vanadium derivatives and/or their salts, to replenish lost catalyst elements and the catalyst is then heated to from 200° to 400° C. in an oxygen-containing oxidizing atmosphere.

PRACTICE OF THE INVENTION

The inventive stabilization and/or reactivation or regeneration of the catalyst system takes place during the oxidation reaction or alternating therewith. The oxidative regeneration of heteropoly acid catalysts during the oxydehydrogenation of isobutyric acid or its esters, or alternating therewith, is described in detail in German patent application 36 26 255. The novel feature, that is, the addition of compounds with catalyst constituents, and more particularly of a molybdenum compound and/or a phosphorus compound, can be implemented with known compounds and by known methods.

Suitable molybdenum compounds are compounds of widely differing valence states, for example, 2, 3, 4 or 6, as well as mixed-valence compounds. Examples are organic compounds of molybdenum, for example, molybdenum(II) acetate, molybdenum oxyacetylates, molybdenum(II) isobutyrate or oxyisobutyrates of molybdenum, also molybdenum acylates or molybdenum oxyacylates, molybdenum alcoholates or oxyalcoholates of molybdenum, or inorganic molybdenum compounds such as $MoO_3$, $Mo(CO)_6$, optionally molybdenum oxyhalides or mixed-valence oxides such as molybdenum blue. The compounds may be introduced into the catalyst-loaded reactor during the regeneration phases, preferably in finely divided form, by mechanical means, or they may be distilled or sublimed into it. For example, when metallic molybdenum is heated to redness in the presence of oxygen-containing gases such as air, sublimable blue molybdenum oxides are formed. Under the conditions prevailing during regeneration, that is, 200° to 400° C., oxidation conditions, and, as already described in German patent application 36 26 255, advantageously the presence of steam, the introduced molybdenum compounds are converted through hydrolytic/oxidative reactions to molybdenum(VI) oxygen compounds, which are particularly useful for the regeneration of heteropoly acid catalysts.

A preferred method of producing molybdenum as a vaporous species in a usable form is to pass isobutyric acid through a bed with an oxidic molybdenum compound such as molybdenum trioxide, $MoO_3$, at temperatures of from 150° to about 350° C. The amount of the entrained molybdenum compounds, for example, oxyisobutyrates of molybdenum, can be controlled through the temperature of the bed. The molybdenum-containing vapor so obtained is optionally mixed at the inlet to the reactor loaded with heteropoly acid catalyst with a further substrate to be reacted (i. e., isobutyric acid) and with an oxygen-containing gas and thus catalytically reacted.

In an advantageous embodiment of this process for the production of vaporous molybdenum compounds suitable for their subsequent inventive use in the vapor-phase oxidation over the catalyst, oxygen in the form of air, for example, and optionally further inert gases as well as steam are passed along with isobutyric acid over the bed containing $MoO_3$, for example. (See also U.S. Pat. No. 4,081,465.) This will prevent inactivation of the source of the molybdenum, for example, $MoO_3$, and hence a reduced or substantially diminished formation of volatile molybdenum compounds. Inactivation of the molybdenum source may be caused by coking of the surfaces of the $MoO_3$, for example, and occasionally also by reduction processes.

The molar ratio of isobutyric acid to oxygen in the gas mixture to be passed over the molybdenum source may vary within wide limits, for example, from 1:0.1 to 1:2, and more particularly from 1:0.5 to 1:1.5. It is determined mainly by the temperature of the bed containing $MoO_3$, for example, through which the gas mixture is passed, which will range from about 150° to about 350° C. On the basis of these parameters, an amount of molybdenum in the form of volatile molybdenum compounds can be produced and continuously adjusted which in accordance with the invention makes up for the loss of molybdenum sustained by the catalyst in the oxidation reactor.

A possible inactivation of the source of molybdenum, for example, $MoO_3$, for the formation of volatile molybdenum compounds as isobutyric acid is being passed over the catalyst at from 150° to 350° C. can also be prevented by alternately passing isobutyric acid, optionally diluted with inert additives, and oxygen in the form of air, for example, over the source of the volatile molybdenum compounds to be formed.

In place of isobutyric acid, other organic compounds, and particularly compounds carrying OH groups, such as acetic acid, or alcohols such as methanol or ethylene glycol, but also acetone, can be used to produce from a source of molybdenum such as $MoO_3$ in particular, by the techniques described, volatile molybdenum compounds which are then introduced in accordance with the invention into the catalytic oxidation reaction, for example, the oxidative dehydrogenation of isobutyric acid.

It has been found that the catalytic effectiveness of the heteropoly acid catalysts can be maintained by adding to them molybdenum in the form of molybdenum compounds in amounts of from 0.003 to 1 gram per kilogram of the organic substance to be reacted over the catalyst during the oxidation reaction, for example, isobutyric acid in its oxidative dehydrogenation to methacrylic acid, either continuously or intermittently at regular or irregular intervals as the catalytic reaction proceeds.

More particularly, for the stabilization or regeneration of the catalyst the molybdenum is introduced in the form of a molybdenum compound, and preferably of a vaporizable organic and/or oxidic compound, into the reactor in amounts of from 0.01 to 0.5 g, and preferably from 0.05 to 0.15 g, per kg of the organic compound to be oxidatively reacted over the catalyst.

For example, from a bed of 24 g of $MoO_3$ with a particle size of from 1 to 3 mm, distributed over a bed length of 15 cm, molybdenum is entrained in amounts of from 0.003 to 1 g per 1,000 kg of isobutyric acid passed over the catalyst, as a function of the temperature of the $MoO_3$ bed and of the partial pressure of the isobutyric acid, as determined in a washing unit located downstream of the $MoO_3$ bed. The determination of the entrained molybdenum is effected by flameless atomic absorption spectrometric analysis from solution.

The inventive entrainment of the catalyst element phosphorus during the oxidation reaction over the heteropoly acid catalyst, preferably in the form of a phosphorus compound, for example, as phosphoric acid or $P_2O_5$, and more particularly as an organic phosphorus compound, and especially one with ester groups, for regeneration can also be carried out with known compounds and by known methods.

Suitable phosphorus compounds are compounds of widely differing valence states of phosphorus, and particularly the trivalent or quinquevalent compounds. Examples are trimethyl phosphite (boiling point, 124° C.), triethyl phosphate (b. p., 215° C.), and especially dimethylmethane phosphonate (b. p., 154° C.). The compounds are introduced in vapor form, preferably continuously and diluted with further components, into the catalyst-loaded reactor, into which they may be distilled or sublimed.

It has been found that the stabilization of the activity and/or the reactivation of the heteropoly acid catalysts is accomplished when during the progress of the catalytic reaction an organic phosphorus compound such as triethyl phosphate or especially dimethylmethane phosphonate is entrained in amounts of from 0.001 to 1.0, and preferably from 0.005 to 0.5, and more particularly from 0.02 to 0.5, parts by weight per 1,000 parts by weight of the organic compound to be reacted, and more particularly of isobutyric acid. Larger amounts of entrained phosphorus compounds result in significant to pronounced deactivation of the catalyst.

Under the conditions prevailing during the oxydehydrogenation, and hence the reactivation, that is, 250° to 400° C., in the presence of oxygen, and, as already described in German patent application 36 26 255, advantageously also in the presence of steam, the phosphorus compounds introduced are possibly reacted further in hydrolytic/oxidative reactions and occasionally converted into phosphorus compounds particularly useful for the regeneration of heteropoly acid catalysts.

When it is necessary to remove spent catalyst from the reactor, or when spent catalyst can be continuously withdrawn from a reactor operated accordingly, for example, a fluidized-bed reactor, then the replenishment of lacking catalyst constituents can be carried out by the addition of appropriate compounds also at temperatures of from 0° to 100° C., and more particularly at normal temperature, that is, at a temperature between about 0° and 50° C. This can be done by mixing spent catalyst with the necessary additives, particularly in the form of the aforesaid compounds, optionally in the presence of water for better distribution of the components to be mixed and ultimately reacted with one another.

The spent catalyst so worked up is then heated in an oxygen-containing oxidizing atmosphere to from 200° to 400° C., the catalyst thus being regenerated rapidly and practically completely. Advantageously but to necessarily, heating to from 200° to 400° C. is carried out in the reactor system to be used in the subsequent catalytic oxidation: A catalyst which has been removed or taken off stream and then replenished with catalytically essential elements is advantageously put on stream continuously in a moving-bed reactor.

The process of the invention permits spent and deactivated molybdo heteropoly acid catalyst to be regenerated and/or maintained fully effective in catalytic vapor-phase oxidations in a much simpler and faster manner than in the prior art.

The process of the invention is of importance in the oxidative dehydrogenation of isobutyric acid or its esters to methacrylic acid or its esters, which is carried out to advantage over catalysts based on heteropoly acids of molybdenum or of salts of such heteropoly acids. The oxydehydrogenation of isobutyric acid, for example, is carried out over these catalysts at temperatures ranging from about 250° to 400° C. in the presence of from 1 to 4 moles of oxygen per mole of isobutyric acid. Further inert gases such as nitrogen or helium, steam, or carbon dioxide may be present. The catalytic reaction may be carried out in fixed-bed reactors, for example, such as tubular reactors, or in moving-bed reactors such as fluidized-bed reactors. (See Ullmanns Enzyklopädie der technischen Chemie, 4th ed., vol. 13, pp. 539–542, Verlag Chemie, Weinheim and New York.)

The catalytic substance is preferably used in the reactor deposited on or diluted with inert materials. (See Ullmanns Enzyklopädie, vol. 13, pp. 558–565.)

In the examples which follow, the invention is illustrated in terms of heteropoly acid catalysts containing P/Mo/V in the oxydehydrogenation of isobutyric acid to methacrylic acid.

EXAMPLES

General oxydehydrogenation test procedure for Examples 1 to 4 and the associated comparative examples.

A vaporous mixture of isobutyric acid, oxygen and nitrogen in a molar ratio of 1:1.5:7.7 is reacted over the catalyst in a circulating reactor according to published German patent application 30 19 731 at 340° C. and with a contact time of 1 second. The space velocity is 1,250 g of isobutyric acid per 1,000 g of catalytic mass and hour. The reaction gas is analyzed continuously by gas chromatography, and from the data so obtained the isobutyric acid conversion and the selectivity for methacrylic acid are determined.

COMPARATIVE EXAMPLE 1

A $Cu_{0.15}H_{3.7}PMo_{11}VO_{40}$ catalyst, prepared according to European patent publication 113,084 and diluted with 30 wt. % of silicic acid (diatomaceous earth:Aerosil®=5:1 parts by weight) resulted in the oxydehydrogenation of isobutyric acid with a selectivity for methacrylic acid of 74% in an isobutyric acid conversion of 82% during the first 25 hours, which then gradually declined and after 96 hours of reaction reached a level of 76.5%.

EXAMPLE 1

A mixture of 141.3 g of a spent $Cu_{0.15}H_{3.7}PMo_{11}V_1O_{40}$ catalyst and 12.1 g $MoO_3$, which corresponded to 38% of the catalytic material lost, was heated to boiling in 1,000 g of water for 2 hours with stirring. The dark-blue suspension was then concentrated by evaporation to give a paste. After 1 hour at 110° C. and 3 hours at 200° C. in a drying oven, the catalyst was heated in the reactor oven for 3 hours at 200° C. in the presence of air. The color of the catalyst then was olive green.

Under the stated reaction conditions, the regenerated catalyst gave the following oxyhydrogenation results:

| Duration of test (hr.) | Conversion (%) |
| --- | --- |
| 25 | 82.2 |
| 48 | 81.1 |
| 82 | 79.9 |
| 109 | 79.1 |

The selectivity for methacrylic acid was 73%.

COMPARATIVE EXAMPLE 2

An $H_5PMo_{10}V_2O_{40}$ catalyst, prepared according to published German patent application 27 22 375 and diluted with 30% of silicic acid (diatomaceous earth:Aerosil®=5:1), was tested under the oxydehydrogenation conditions stated.

| Duration of test (hr.) | Conversion (%) |
| --- | --- |
| 6 | 81.4 |
| 23 | 79.2 |
| 49 | 79.0 |
| 72 | 77.1 |

The selectivity for methacrylic acid was 72%.

EXAMPLE 2

A mixture of 164.2 g of a spent $H_5PMo_{10}V_2O_{40}$ catalyst and 11.2 g of $MoO_3$, which corresponded to 100% of the material lost, was heated to boiling in 1,578 g of water for 6 hours with stirring. After the addition of 5% of Aerosil®, the dark-blue mixture was concentrated by evaporation to give a paste. The preparation was then heated for 1 hour at 110° C. and for 3 hours at 200° C. in a drying oven. The oxidation was carried out at 300° C. in the reactor oven for 3 hours while air was being passed through it.

Under the reaction conditions of the catalyst from Comparative Example 2, the regenerated catalyst gave the follow results:

| Duration of test (hr.) | Conversion (%) |
| --- | --- |
| 7 | 80.6 |
| 27 | 79.8 |
| 72 | 77.5 |

The selectivity for methacrylic acid was 72%.

COMPARATIVE EXAMPLE 3

A $Cu_{0.2}H_{4.6}PMo_{10}V_2O_{40}$ catalyst diluted with 30% silicic acid (diatomaceous earth:Aerosil®=5:1) was tested under the oxydehydrogenation conditions stated. Results:

| Duration of test (hr.) | Conversion (%) |
| --- | --- |
| 7 | 78.2 |
| 26 | 72.9 |
| 49 | 69.6 |
| 78 | 64.7 |

The selectivity for methacrylic acid was 75%.

EXAMPLE 3

A mixture of 166.2 g of a spent $Cu_{0.2}H_{4.6}PMo_{10}V_2O_{40}$ catalyst and 6.7 g of $MoO_3$, which corresponded to 90% of the catalytic material lost, was heated to boiling in 1,550 g of water for 6 hours with stirring.

Then 5 wt. % of Aerosil® was added and the mixture was concentrated by evaporation to give a paste. After 1 hour at 110° C. and 3 hours at 200° C. in a drying oven, the catalyst was oxidized for 3 hours in a muffle furnace at 310° C. After being worked up, the catalyst had an olive green color. Under the reaction conditions of the catalyst from the Comparative Example, the regenerated catalyst gave the following results:

| Duration of test (hr.) | Conversion (%) |
| --- | --- |
| 6 | 77.5 |
| 27 | 76.3 |
| 80 | 75.5 |

The selectivity for methacrylic acid was 73%.

COMPARATIVE EXAMPLE 4

A $Cu_{0.1}Cs_1H_{2.8}PMo_{11}V_1O_{40}$ catalyst diluted with 30% silicic acid (diatomaceous earth:Aerosil®=5:1) was tested under the oxydehydrogenation conditions stated. Results:

| Duration of test (hr.) | Conversion (%) |
| --- | --- |
| 6 | 82.2 |
| 25 | 79.8 |
| 73 | 76.4 |

The selectivity for methacrylic acid was 75%.

EXAMPLE 4

A mixture of 90.3 g of a spent $Cu_{1.0}Cs_1H_{2.8}PMo_{11}V_1O_{40}$ catalyst and 11.9 g of $MoO_3$, which corresponded to 90% of the catalytic material lost, was heated to boiling in 920 g of water for 1 hour with stirring.

The mixture was then concentrated by evaporation to give a paste. After 1 hour at 110° C. and 3 hours at 200° C. in a drying oven, the catalyst was oxidized for 3 hours in a muffle furnace at 280° C. After being worked up, the catalyst had an olive green color.

Under the reaction conditions of the catalyst from the Comparative Example, the regenerated catalyst gave the following results:

| Duration of test (hr.) | Conversion (%) |
| --- | --- |
| 20 | 82.3 |
| 43 | 81.8 |
| 67 | 81.4 |

The selectivity for methacrylic acid was 74%.

EXAMPLE 5

(a) Comparison

When 1.5 moles per hour of a gas mixture of 0.06 mole of nitrogen, 1.155 moles of helium, 0.045 mole of isobutyric acid and 0.24 mole of oxygen is passed at 316° C. and a pressure of 1 bar over 2 g of $H_6V_3Mo_9PO_{40}$ of a particle size of from 400 to 600 microns, diluted with glass spherules of the same particle size in a weight ratio of 1:4 and distributed over a bed length of 10 cm, 88% of the isobutyric acid introduced is initially converted, as gas-chromatographic analysis will show. In the process, methacrylic acid is formed in a yield of 60% of theory, that is, with a selectivity of 68%. The activity of the catalyst drops steadily in the course of a reaction time of 20 hours, after which, with constant selectivity, the isobutyric acid conversion will decrease to 66%.

(b) Procedure according to the invention

Now when the gas mixture described under (a), but without the oxygen, is first passed over 24 g of $MoO_3$, maintained at 250° C., and after leaving the $MoO_3$ zone (the "Mo saturator") is mixed with the amount of oxygen specified under (a) and the mixture so prepared is reacted as described in (a), no drop in activity will be observed during a reaction time of 25 hours. With an isobutyric acid conversion of 88%, methacrylic acid will be obtained in a yield of 61% of theory at a constant selectivity of 69%.

EXAMPLE 6

Over 2 g of $H_5V_2Mo_{10}PO_{40}$, disposed like the homologous acid catalyst in Example 5, there was passed at 309° C. 1.5 moles per hour of a gas mixture consisting of (a) 0.06 mole of nitrogen, 1.125 moles of helium and 0.075 mole of isobutyric acid loaded with molybdenum by the procedure described in Example 5 (b), and of (b) 0.24 mole of oxygen.

During a reaction time of 60 hours, a constant isobutyric acid conversion of 84% and a constant methacrylic acid yield of 53% of theory, corresponding to a selectivity of 63%, were determined by gas-chromatographic analyses.

Without entrainment of molybdenum from the $MoO_3$ reactor (the "Mo saturator"), the activity of the catalyst decreases markedly even during the first 10 hours of reaction, with the isobutyric acid conversion reaching a level of 66%.

EXAMPLE 7

An $H_5V_2Mo_{10}PO_{40}$ catalyst disposed as described in Examples 5 and 6 gives a methacrylic acid yield of 48% of theory even after a reaction time of 220 hours in the oxyhydrogenation of isobutyric acid to methacrylic acid. Over the next 30 hours of reaction, the yield drops to 24% of theory. Now the oxygen-free portion of the gas mixture described in Example 6 is fed into the $MoO_3$ reactor, maintained at 320° C., and the Mo-containing gas mixture leaving the reactor is mixed with the amount of oxygen specified in Example 6. Gas-chromatographic analysis shows that no further deactivation of the catalyst occurs during a further 20 hours of reaction.

EXAMPLE 8

Over 59 kg of a heteropoly acid catalyst prepared from 12 wt. % of $H_{3.6}Cu_{0.2}Mo_{11}PVO_{40}$ and 88 wt. % of an $Al_2O_3$ carrier, 18,300 liters per hour of a gas mixture consisting of isobutyric acid, oxygen, nitrogen and water in a molar ratio of 1:1.5:5.64:1 was passed at a catalyst temperature of 350° C.

During an operating time of 550 hours, a steady drop in isobutyric acid conversion from initially 95% to 73% was determined by gas-chromatographic analyses. During this operating time, the selectivity for methacrylic acid decreased from initially 70% to 65%.

At that point in time, 4 g of dimethylmethane phosphonate was added to the gas mixture in the first hour. Then a gas mixture comprising, in contrast with the above data, isobutyric acid containing 0.01 wt. % of dimethylmethane phosphonate was passed over the catalyst over a 500-hour period. As a result of these steps, the conversion of isobutyric acid increased within a few hours to 80% and then remained constant, like the selectivity for methacrylic acid at 65%, throughout the operating time.

When the addition of the phosphorus compound is omitted, the isobutyric acid conversion drops to about 60% in the course of the reaction time of approximately 1,000 hours, and the selectivity for methacrylic acid to about 50%.

EXAMPLE 9

In a further test in a laboratory reactor with 2 kg of the same catalyst as in Example 8, at a reaction temperature of 360° C. and a flow rate of 620 liters per hour of a gas mixture consisting of isobutyric acid, oxygen, nitrogen and water in a molar ratio of 1:1.5:5.64:1, a 7% decrease in the isobutyric acid conversion and an 18% drop in the selectivity for methacrylic acid to 52% were determined by gas-chromatographic analyses over an operating time of 1,465 hours. Then 1.74 g of dimethylmethane phosphonate was passed over the catalyst for 46 hours with the gas mixture. In this way, the initial activity was restored to an isobutyric acid conversion of 90%, and the selectivity for methacrylic acid rose to 66%. Example 10

In a test conducted as in Example 9, after the isobutyric acid conversion had dropped from 90% to 60% and the selectivity for methacrylic acid from 70% to 43.3% during a reaction time of 1,006 hours, dimethylmethane phosphonate was added to the gas mixture at the rate of 0.1 wt. %, based on the isobutyric acid. A brief initial restoration of catalyst activity and selectivity was followed by a complete loss of catalyst activity and selectivity as the cumulative phosphorus dose increased. This shows that the amount of dimethylmethane phosphonate metered in was too high.

We claim:

1. A method for the vapor phase oxydehydrogenation of isobutyric acid or a lower alkyl ester thereof to form methacrylic acid or a lower alkyl ester thereof, respectively, which method comprises passing said isobutyric acid or lower alkyl ester thereof over a catalyst selected from the group consisting of heteropolyphosphoric acids of molybdenum, molybdovanadophosphoric acids, and such acids containing a further metallic element as a cation, at a temperature from 250° C. to 400° C. in the presence of an oxidizing atmosphere containing oxygen, while introducing vapors of at least one compound selected from the group consisting of compounds of molybdenum and compounds of phosphorus.

2. A method as in claim 1 wherein said metallic element is selected from the group consisting of metallic elements of Group I to Group VII elements in the periodic table.

3. A method as in claim 1 wherein said metallic element is selected from the group consisting of Li, Na, K, Rb, Cs, Cu, Mg, Zn, Cd, In, Tl, V, Bi, Mo, Cr, Te, Fe, Co, and Ni.

4. A method as in claim 1 wherein said metallic element is selected from the group consisting of Cu and Cs.

5. A method as in claim 1 wherein said vapors are vapors of a compound of molybdenum introduced in an amount from 0.003 gram to 1 gram per 1000 grams of said isobutyric acid or lower alkyl ester thereof.

6. A method as in claim 5 wherein said vapors are generated by passing isobutyric acid over a molybdenum oxide at a temperature from 100° C. to 350° C.

7. A method as in claim 6 wherein said molybdenum oxide is molybdenum trioxide, $MoO_3$.

8. A method as in claim 5 wherein said isobutyric acid is admixed with oxygen.

9. A method as in claim 5 wherein isobutyric acid and oxygen are alternatively passed over said molybdenum oxide.

10. A method as in claim 5 wherein said vapors are generated by passing a member selected from the group consisting of acetic acid, an alcohol, or acetone over a molybdenum oxide at a temperature from 100° C. to 350° C.

11. A method as in claim 1 wherein said vapors are vapors of a compound of phosphorus introduced in an amount from 0.001 gram to 1.0 gram per 1000 grams of said isobutyric acid or ester thereof.

12. A method as in claim 11 wherein said compound of phosphorus is dimethylmethane phosphonate.

* * * * *